United States Patent [19]

Kabalnov et al.

[11] Patent Number: 5,804,162
[45] Date of Patent: Sep. 8, 1998

[54] GAS EMULSIONS STABILIZED WITH FLUORINATED ETHERS HAVING LOW OSTWALD COEFFICIENTS

[75] Inventors: Alexey Kabalnov; Ernest George Schutt; Jeffry Greg Weers, all of San Diego, Calif.

[73] Assignee: Alliance Pharmaceutical Corp., San Diego, Calif.

[21] Appl. No.: 479,621

[22] Filed: Jun. 7, 1995

[51] Int. Cl.⁶ .......................... A61K 49/00; G01N 31/00; G01N 33/48
[52] U.S. Cl. .......................... 424/9.51; 424/9.5; 424/450; 128/662.02
[58] Field of Search .................... 424/9.3, 9.32, 424/9.5, 9.51, 400, 450, 9.2, 9.52; 252/302, 350; 128/662.02

[56] References Cited

U.S. PATENT DOCUMENTS

| | | |
|---|---|---|
| 4,276,885 | 7/1981 | Tickner et al. . |
| 4,466,442 | 8/1984 | Hilmann et al. . |
| 4,613,326 | 9/1986 | Szwarc . |
| 4,657,756 | 4/1987 | Rasor et al. . |
| 4,684,479 | 8/1987 | D'Arrigo . |
| 4,718,433 | 1/1988 | Feinstein . |
| 4,774,958 | 10/1988 | Feinstein . |
| 4,832,941 | 5/1989 | Berwing et al. . |
| 4,844,882 | 7/1989 | Widder et al. . |
| 4,859,363 | 8/1989 | Davies et al. ............... 252/312 |
| 4,898,734 | 2/1990 | Mathiowitz et al. . |
| 4,904,479 | 2/1990 | Illum . |
| 4,925,678 | 5/1990 | Ranney . |
| 4,927,623 | 5/1990 | Long Jr. . |
| 4,957,656 | 9/1990 | Cerny et al. . |
| 5,088,499 | 2/1992 | Unger . |
| 5,108,759 | 4/1992 | Ranney . |
| 5,123,414 | 6/1992 | Unger . |
| 5,141,738 | 8/1992 | Rasor et al. . |
| 5,149,319 | 9/1992 | Unger . |
| 5,155,215 | 10/1992 | Ranney . |
| 5,186,922 | 2/1993 | Shell et al. . |
| 5,196,183 | 3/1993 | Yudelson et al. . |
| 5,205,287 | 4/1993 | Erbel et al. . |
| 5,205,290 | 4/1993 | Unger . |
| 5,271,928 | 12/1993 | Schneider et al. . |
| 5,305,757 | 4/1994 | Unger et al. . |
| 5,310,540 | 5/1994 | Giddey et al. . |
| 5,315,997 | 5/1994 | Widder et al. . |
| 5,315,998 | 5/1994 | Tachibana et al. . |
| 5,333,613 | 8/1994 | Tickner et al. . |
| 5,334,381 | 8/1994 | Unger . |
| 5,348,016 | 9/1994 | Unger et al. . |
| 5,350,571 | 9/1994 | Kaufman et al. ............ 424/9.1 |
| 5,352,435 | 10/1994 | Unger . |
| 5,352,436 | 10/1994 | Wheatley et al. . |
| 5,376,380 | 12/1994 | Kikuchi et al. . |
| 5,380,519 | 1/1995 | Schneider et al. . |
| 5,393,524 | 2/1995 | Quay . |
| 5,439,669 | 8/1995 | Kaufman et al. ............ 424/9.5 |
| 5,498,421 | 3/1996 | Grinstaff et al. ............ 424/450 |
| 5,501,863 | 3/1996 | Rössling et al. ............ 424/489 |
| 5,502,094 | 3/1996 | Moore et al. ............... 524/145 |
| 5,536,489 | 7/1996 | Lohrmann et al. ........... 424/9.52 |
| 5,542,935 | 8/1996 | Unger et al. ............... 424/450 |
| 5,556,610 | 9/1996 | Yan et al. ................. 424/9 |
| 5,558,094 | 9/1996 | Quay ..................... 128/662.02 |
| 5,558,853 | 9/1996 | Quay ..................... 424/9 |
| 5,558,854 | 9/1996 | Quay ..................... 424/9 |
| 5,558,855 | 9/1996 | Quay ..................... 424/9 |
| 5,558,856 | 9/1996 | Klaveness et al. ........... 424/9.37 |
| 5,558,857 | 9/1996 | Klaveness et al. ........... 424/9.52 |
| 5,562,893 | 10/1996 | Lohrmann ................. 424/9.52 |

FOREIGN PATENT DOCUMENTS

| | | |
|---|---|---|
| WO8906978 | 8/1989 | Australia . |
| 652803B | 9/1994 | Australia . |
| 0123235 | 10/1984 | European Pat. Off. . |
| 0131540A2 | 1/1985 | European Pat. Off. . |
| 0231091 | 8/1987 | European Pat. Off. . |
| 0279379 | 8/1988 | European Pat. Off. . |
| 0586875A1 | 2/1989 | European Pat. Off. . |
| 0320433A3 | 6/1989 | European Pat. Off. . |
| 0359246 | 3/1990 | European Pat. Off. . |
| 0052575 | 5/1992 | European Pat. Off. . |
| 0554213 | 8/1993 | European Pat. Off. . |
| 0606613A1 | 7/1994 | European Pat. Off. . |
| 0458745B1 | 9/1994 | European Pat. Off. . |
| 0638318A2 | 2/1995 | European Pat. Off. . |

(List continued on next page.)

OTHER PUBLICATIONS

K. Bergh, et al., "Variability Over Time of Complement Activation Induced by Air Bubbles in Human and Rabbit Sera", *J. Appl. Physiol.*, 74(4):1811–1815, 1993.

K.A. Shastri, et al., "In Vitro Activation of Human Complement by Nitrogen Bubbles", *Undersea Biomedical Research*, 18(3):157–165, 1991.

N. de Jong, et al., "Principles and Recent Developments in Ultrasound Contrast Agents", *Ultrasonics*, 29:324–330, 1991.

Greer, "First Untrasound Contrast Agent Awaits OK From FDA", *Advance for Radiologic Science Professionals*, pp. 3–5, 1993.

Mattrey, R.F., M.D., Perfluoroctylbromide: A Liver/Spleen–Specific and Tumor–Imaging Ultrasond Contrast Material, *RADIOLOGY* 145(3):759–762 (Dec. 1992).

(List continued on next page.)

*Primary Examiner*—John Kight
*Assistant Examiner*—Dameron Jones
*Attorney, Agent, or Firm*—Knobbe, Martens, Olson & Bear LLP

[57] ABSTRACT

Long lasting gas emulsions for ultrasound and magnetic resonance imaging contrast enhancement utilize low Ostwald coefficient fluoromono- and fluoropolyether compounds. Gas emulsion preparations are disclosed containing air mixed with perfluorodiglyme ($CF_3(OCF_2CF_2)_2OCF_3$), perfluoromonoglyme ($CF_3OCF_2CF_2OCF_3$), perfluorodiethylether, $C_2F_5OC_2F_5$, perfluoroethylmethylether, $CF_3OC_2F_5$, and perfluorodimethylether, $CF_3OCF_3$.

89 Claims, 1 Drawing Sheet

5,804,162
Page 2

FOREIGN PATENT DOCUMENTS

| | | |
|---|---|---|
| 4406474 | 8/1995 | Germany . |
| WO8905160 | 6/1989 | WIPO . |
| WO 91/09629 | 7/1991 | WIPO . |
| WO 91/12823 | 9/1991 | WIPO . |
| WO 91/15999 | 10/1991 | WIPO . |
| 9211873 | 7/1992 | WIPO . |
| WO9300930 | 7/1992 | WIPO . |
| WO 92/22247 | 12/1992 | WIPO . |
| WO922249 | 12/1992 | WIPO . |
| WO 93/02712 | 2/1993 | WIPO . |
| WO9303671 | 3/1993 | WIPO . |
| WO 93/05819 | 4/1993 | WIPO . |
| WO 93/06869 | 4/1993 | WIPO . |
| WO9325242 | 12/1993 | WIPO . |
| WO9401140 | 1/1994 | WIPO . |
| WO9406477 | 3/1994 | WIPO . |
| WO9408707 | 4/1994 | WIPO . |
| WO9409703 | 5/1994 | WIPO . |
| WO9409829 | 5/1994 | WIPO . |
| WO9416739 | 8/1994 | WIPO . |
| 9421301 | 9/1994 | WIPO . |
| WO9421175 | 9/1994 | WIPO . |
| WO9428797 | 12/1994 | WIPO . |
| WO9428939 | 12/1994 | WIPO . |
| WO9516467 | 6/1995 | WIPO . |
| 9609793 | 4/1996 | WIPO . |
| 9626746 | 9/1996 | WIPO . |
| 9628090 | 9/1996 | WIPO . |

OTHER PUBLICATIONS

Kabalnov, et al. "Phospholipids as Emulsion Stabilizers. 1. Interfacial Tensions" Langmuir 11(8): 2966–2974 (May 15, 1995).

Kitagawa, et al. Biological Abstracts 63: 6392 (1977).

Keough, et al. Biological Abstracts 81: 105308 (1986).

Matsuda, et al. "Contrast Echocardiography of the Left Heart by Intravenous Injection of Perfluorochemical Emulsion" J. of Cardiography 13(4): 1021–1028 (1983).

Sunamoto, et al. "Liposomal Membranes" J. Biochem 88: 1219–1226 (1980).

Davies et al (1981), Journal of Colloid and Interface Science, vol. 80, No. 2, pp. 508–511, "Ostwald Ripening and the Stability of Emulsion Systems: an Explanation for the Effect of an Added Third Component".

Fig. 1

GAS EMULSIONS STABILIZED WITH FLUORINATED ETHERS HAVING LOW OSTWALD COEFFICIENTS

BACKGROUND OF THE INVENTION

1. Field of the Invention

The present invention includes a method for preparing stable, long-lived gas emulsions for ultrasound contrast enhancement and other uses, and to compositions of the gas emulsions so prepared.

2. Background of the Art

Ultrasound technology provides an important and more economical alternative to imaging techniques which use ionizing radiation. While numerous conventional imaging technologies are available, e.g., magnetic resonance imaging (MRI), computerized tomography (CT), and positron emission tomography (PET), each of these techniques use extremely expensive equipment. Moreover, CT and PET utilize ionizing radiation. Unlike these techniques, ultrasound imaging equipment is relatively inexpensive. Moreover, ultrasound imaging does not use ionizing radiation.

Ultrasound imaging makes use of differences in tissue density and composition that affect the reflection of sound waves by those tissues. Images are especially sharp where there are distinct variations in tissue density or compressibility, such as at tissue interfaces. Interfaces between solid tissues, the skeletal system, and various organs and/or tumors are readily imaged with ultrasound.

Accordingly, in many imaging applications ultrasound performs suitably without use of contrast enhancement agents; however, for other applications, such as visualization of flowing blood, there have been ongoing efforts to develop such agents to provide contrast enhancement. One particularly significant application for such contrast agents is in the area of perfusion imaging. Such ultrasound contrast agents could improve imaging of flowing blood in the heart muscle, kidneys, liver, and other tissues. This, in turn, would facilitate research, diagnosis, surgery, and therapy related to the imaged tissues. A blood pool contrast agent would also allow imaging on the basis of blood content (e.g., tumors and inflamed tissues) and would aid in the visualization of the placenta and fetus by enhancing only the maternal circulation.

A variety of ultrasound contrast enhancement agents have been proposed. The most successful have generally consisted of dispersions of small bubbles of gas that can be injected intravenously. The bubbles are injected into the bloodstream of a living body to be imaged thereby providing an emulsion in the flowing blood that is of a different density and a much higher compressibility than the surrounding fluid tissue and blood. As a result, these bubbles can easily be imaged with ultrasound.

Unfortunately, the creation of bubbles that are effective ultrasound scatterers in vivo has been difficult. Several explanations are apparent. First, such bubbles tend to shrink rapidly due to the diffusion of the trapped gas into the surrounding liquid. This is especially true of bubbles containing air or its component gases (such as nitrogen) which are highly soluble in water. It might be expected that bubble lifetime could be improved by simply increasing the size of the bubbles so more gas needs to escape before the bubbles disappear. This approach has proven unsatisfactory, however, because bubbles larger than about 10 μm in diameter are cleared from the bloodstream by the lungs, preventing their further circulation. Additionally, larger bubbles are not capable of circulating through smaller blood vessels and capillaries.

Microbubbles with satisfactory in vivo performance should also posses advantageous biological characteristics. First, the compounds making up the gas inside the microbubbles should be biocompatible. Ultimately, the microbubbles containing the gas phase will decay and the gas phase will be released into the blood either as a dissolved gas or as submicron droplets of the condensed liquid. Therefore, the gases will primarily be removed from the body through lung respiration or through a combination of respiration and other metabolic pathways in the reticuloendothelial system. Even when bubble persistence is sufficient to allow for several passes through the circulatory system of an animal or human, microbubble uptake by the reticuloendothelial phagocytic cells of the liver can limit the effectiveness of the contrast agent. Adverse immune system reactions can also reduce the in vivo lifetimes of the bubble, and should be avoided. For example, "naked" microbubbles have been shown to produce adverse responses such as the activation of complement (See, for example, K. A. Shastri et al. (1991) *Undersea Biomed. Res.,* 18, 157). However, as known in the art, these undesired responses may be reduced through the use of appropriate encapsulating agents.

Accordingly, efforts to improve the in vivo lifetime, of microbubbles have included the use of stability, and hence the various encapsulating materials. For instance, gelatins or albumin microspheres that are initially formed in liquid suspension, and which entrap gas during solidification, have been used. The use of surfactants as stabilizing agents for gas bubble dispersions has also been explored, as in U.S. Pat. Nos. 4,466,442 to Hilmann et al., and 5,352,436 to Wheatley et al. Some surfactant-containing contrast enhancement agents entrap gas bubbles in the aqueous core of liposomes as in U.S. Pat. No. 5,334,381 to Unger and U.S. Pat. No. 4,900,540 to Ryan et al.

Recently, the affects of the entrapped gas on bubble lifetime has received considerable attention. Aside from air and its components, various noble gases such as krypton and argon have been used. Attention has now focused on biocompatible gases which have low water solubilities. Low solubility has been shown theoretically to be an important factor in gas bubble stability. In Epstein and Plesset, On the Stability of Gas Bubbles in Liquid-Gas Solutions, (1950) *J. Chem. Phys.* 18(11), 1505–1509, the rate of gas bubble shrinkage was derived as a function of gas density, solubility, and diffusivity in the surrounding medium. The stability of liquid-liquid emulsions has also been shown to increase with the decreasing solubility of the dispersed phase (Kabalnov and Shchukin, Ostwald Ripening Theory: Applications to Fluorocarbon Emulsion Stability, *Advances in Colloid and Interface Science,* 38:69–97, 1992).

With certain simplifying assumptions, the Epstein and Plesset formula leads to the formula for bubble lifetime (τ) given by Quay in U.S. Pat. No. 5,393,524:

$$\tau \alpha \rho/DC \qquad (1)$$

where ρ is the density of the entrapped gas, D is the diffusivity of the gas in the surrounding medium, and C is the solubility of the gas in the surrounding medium. Based on this formula, Quay forms bubbles using gases selected on the basis of being a gas at atmospheric pressure and body temperature (37° C.) and having reduced water solubility, higher density, and reduced gas diffusivity in solution in comparison to air. In the same vein, Schneider et al. in EP0554213A1 disclose gases chosen on the basis of low water solubility and high molecular weight. Specifically disclosed gases include $SF_6$, and $SeF_6$, as well as various perfluorinated hydrocarbons.

Although reduced water solubility and diffusivity can affect the rate at which the gas leaves the bubble (as originally predicted by Epstein and Plesset), the Quay and Schneider gas selection criteria are inaccurate in that they result in the inclusion of certain unsuitable gases and the exclusion of certain optimally suitable gases. For example, in U.S. Pat. No. 5,393,524, Quay suggests choosing microbubble gases based on a calculation of the Q value for the proposed gas, wherein:

$$Q = 4 \times 10^{-7} \times \rho/DC, \qquad (2)$$

$\rho$ is the gas density ($kg/m^3$), C is the water solubility of the gas (M), and D is the diffusivity of the gas in solution ($cm^2/s$). Quay teaches that the Q value should be at least 30 to be a useful gas for ultrasound contrast enhancement. A simple estimate using literature water solubility data (E. Wilhelm, R. Battino, and R. J. Wilcock, Chemical Reviews, 1977, v. 77, p. 219) shows that the Q values of virtually all known gases (with the exception of hydrogen and helium) approach or exceed this value. At 25 degrees C., oxygen, for example, has a Q of 20, and nitrogen has a Q of 35. The Quay disclosure, therefore, provides little guidance for the selection of effective microbubble gases.

Moreover, the Quay's Q coefficient criterion as well as Schneider's disclosure in EP0554213A1 fail to consider certain major causes of bubble shrinkage, namely, the effects of bubble surface tension, surfactants and gas osmotic effects, and the potential for filling gas condensation into a liquid. Namely, the partial pressure of the filling gas must be high enough to oppose the excess Leplace overpressure inside the bubbles. If the saturated vapor pressure is low the filling gas may condense into liquid and contrast ability will be lost. Accordingly, a need exists in the art for stabilized contrast enhancement agents that are biocompatible, easily prepared, and provide superior in vivo contrast enhancement in ultrasound imaging. A need also exists for methods to prepare and use such contrast enhancement agents.

SUMMARY OF THE INVENTION

The present invention utilizes low Ostwald coefficient fluoroether compounds to provide long lasting gas emulsions for ultrasound and magnetic resonance imaging contrast enhancement. When microbubble preparations are prepared using the compounds of the present invention, longer lasting images of the heart and other internal organs may be obtained than has been before possible. In this invention, gas emulsions comprising a previously unconsidered class of compounds which combine a reduced water solubility without a significantly reduced saturated vapor pressure (and thus surprisingly low Ostwald coefficients) are disclosed. The high vapor pressure additionally helps to reduce the loss of contrast due to the filling gas condensation into liquid. These compounds are the fluorinated mono- and polyethers. When perfluoropolyethers are compared with their perfluorocarbon analogues with the same number of carbonatoms, adding ether oxygen does not affect the vapor pressure significantly, whilst the water solubility decreases by a factor of approximately 2–3.

Thus, a gas emulsion for ultrasound contrast enhancement comprising a plurality of gas bubbles in a liquid medium, with the gas comprising a fluoromono- or fluoropolyether, or a mixture thereof is disclosed. In some embodiments, the gas comprises a compound having an Ostwald coefficient of less than about $100 \times 10^{-6}$ at 37 degrees C., leading to especially long in vivo contrast enhancement. Vapor of perfluorodiethylether, perfluorodimethylether, perfluoromethylethylether, perfluoromonoglyme, perfluorodiglyme has been found to be especially advantageous.

The gas bubbles of the present invention may be surrounded by a surfactant layer which preferably comprises a first and a second surfactant, the first surfactant consisting essentially of a phospholipid or mixture of phospholipids having at least one acyl chain which comprises at least 10 carbon atoms, and comprising at least about 5% w/w of total surfactant, with the second surfactant being more water soluble than the first surfactant. Most preferably, the first surfactant comprises a phosphatidylcholine with one or more acyl chains, at least one chain comprising 12 to 18 carbon atoms, and said second surfactant comprises a phosphatidylcholine with one or more acyl chains, at least one chain comprising 6 to 12 carbon atoms.

DETAILED DESCRIPTION OF THE INVENTION

I. General

As used herein, microbubbles are considered to be bubbles of gas in an aqueous medium having a diameter between about 0.5 and 300 $\mu$m, preferably having a diameter no more than about 200, 100, or 50 $\mu$m. Microbubbles may or may not have a layer or coating at the gas/liquid interface. If present, the coating may be one or more molecules thick. Additionally, microbubbles may be trapped by a bimolecular layer (as in the case of unilamellar liposomes), or may be trapped by several layers of bilayers (multilamellar vesicles). Microbubbles may also be surrounded by more permanent shell-like structures such as denatured proteins. As emulsions are generally characterized as a dispersion of two or more immiscible fluids stabilized by a surfactant interface, the surfactant containing embodiments of the present invention are in essence gas emulsions, with the discontinuous phase of the emulsion being a gas, rather than a liquid. Consequently, the term gas emulsion, as used herein, means a dispersion of a plurality of microbubbles of gas in an aqueous medium.

For intravascular use, optimum bubble size is determined by two competing concerns. Smaller bubbles are effective in circulating through small blood vessels and capillaries, but ultrasound echogenicity is strongly dependent upon bubble size. Suitable microbubbles for vascular ultrasound contrast enhancement are therefore preferably about 1–10 $\mu$m in diameter, with 3–5 $\mu$m especially preferred.

II. Selecting Microbubble Gases and Gas Combinations

The short lifetime of most microbubble preparations is caused in part by the increased gas pressure inside the bubble, which results from the surface tension forces acting on the bubble. This elevated internal pressure increases as the diameter of the bubble is reduced. The increased internal gas pressure forces the gas inside the bubble to dissolve, resulting in bubble collapse as the gas is forced into solution.

The Laplace equation, $\Delta P=2\sigma/r$, (where $\Delta P$ is the increased gas pressure inside the bubble, $\sigma$ is the surface tension of the bubble film, and r is the radius of the bubble) describes the pressure exerted on a gas bubble by the surrounding bubble surface or film. The Laplace pressure is inversely proportional to the bubble radius; thus, as the bubble shrinks, the Laplace pressure increases, increasing the rate of diffusion of gas out of the bubble and the rate of bubble shrinkage.

Quay's formula for bubble lifetime (Equation 1) ignores this factor. Different conclusions regarding gas suitability result when one considers the effect of the bubble Laplace pressure in conjunction with the fact that the blood naturally contains certain gases, such as nitrogen, at near atmospheric pressure. More specifically, it leads to the conclusion that a gas mixture of a "primary modifier gas" such as nitrogen, or air, or another gas naturally abundant in the blood, in combination with a "gas osmotic agent" of low water solubility and high vapor pressure results in optimum bubble lifetime. Some embodiments of such gas mixtures are described in co-pending U.S. patent application Ser. Nos. 08/099,951; 08/284,083; and 08/395,680 herein incorporated by reference.

The stabilizing influence of proper gas combinations can be understood more readily through a discussion of certain hypothetical bubbles in aqueous solution. The bubbles discussed may all be considered to be surrounded by a layer of surface tension reducing surfactant. However, the effects of gas or gas combinations with differing solubilities, surfactant membrane layer permeabilities, and external concentrations will be considered.

The physical interactions of the primary modifier gas, secondary osmotic agent, and medium can be incorporated into a general theory of bubble behavior. In a solution containing a relatively high concentration of the primary modifier gas (as compared to the concentration in solution of the gas osmotic agent), bubble lives can be determined theoretically as a function of certain physical characteristics of the secondary gas osmotic agent.

Consider a microbubble of radius r, containing two ideal gases: air (nitrogen) ($n_a$ moles) and osmotic agent ($n_F$ moles). The microbubble is in an infinite water medium, which contains no osmotic agent and is saturated with an infinite supply of air. Air is much more soluble in water and diffuses quickly out of the microbubble. Treating the microbubble in a manner analogous to a semipermeable membrane, we may consider that the chemical potential of air in the microbubble is the same as in the infinity, whereas the chemical potential of the fluorocarbon in the microbubble is higher than that in the infinity. Mechanical equilibration to the pressure gradient across the interface is assumed to be fast. Thus, it is the diffusion of osmotic agent out of the microbubble that determines the microbubble lifetime. The pressure inside the microbubble is the sum of the partial pressures of the air and the fluorocarbon:

$$p^b = p_F^b + p_a^b \tag{3}$$

Because air is very soluble in the water medium, and diffuses into and out of the bubble quickly, net mass flow of air is small, and the partial pressure of the air inside the microbubble is approximately equal to the atmospheric air pressure applied to the water medium. This means that the excess Laplace pressure is due to osmotic agent only:

$$p_F^b = \frac{2\sigma}{r} = \frac{n_F}{\frac{4}{3}\pi r^3} RT \tag{4}$$

Furthermore, the steady-state diffusional mass flow J (mol/s) of the osmotic agent from a spherical particle into the medium with zero concentration in the medium is equal to:

$$J = 4\pi r^2 D \frac{c_{F,subsurf}}{r} \tag{5}$$

Here D is the osmotic agent-in-water diffusion coefficient, and $c_{F,subsurf}$ is the equilibrium subsurface osmotic agent-in-water concentration. We assume the subsurface osmotic agent concentration in water to be in equilibrium with the fluorocarbon in the microbubble. Because the vapor is undersaturated, the subsurface concentration of the microbubble osmotic agent is lower than its saturated concentration, and is related to the internal osmotic agent vapor pressure as follows:

$$c_{F,subsurf} = c_{F,sat}(T) \frac{p_F^b}{p_{F,sat}(T)} = c_{F,sat}(T) \frac{2\sigma}{p_{F,sat}(T)r} \tag{6}$$

From Equations 4, 5, and 6, it follows that:

$$\frac{d}{dt} r^2 = 3DRT \frac{c_{F,sat}}{p_{F,sat}} \tag{7}$$

Note that the combination $$RT \frac{c_{F,sat}}{p_{F,sat}}$$

is dimensionless and has within it the ratio of the saturated osmotic agent vapor pressure to the corresponding equilibrium osmotic agent water solubility. This ratio is known as the Ostwald coefficient (often denoted "L"). The square of the microbubble radius decreases with time at a rate proportional to the Ostwald coefficient of the gas osmotic agent. Accordingly, gas osmotic agents with low Ostwald coefficients provide superior bubble longevity. The Ostwald coefficient of the gas osmotic agent is preferably less than about $500\times10^{-6}$, $100\times10^{-6}$, or $50\times10^{-6}$, most preferably less than about $40\times10^{-6}$, $30\times10^{-6}$, $20\times10^{-6}$, $10\times10^{-6}$, $5\times10^{-6}$, or $1\times10^{-6}$.

TABLE 1

Otswald coefficients and vapor pressures at 25° C.

| filling gas | b. p., °C.[1] | $P_{F,sat}^3$ atm[2] | $L \times 10^6$ [3] |
|---|---|---|---|
| $O_2$ | −183 | | 31110 |
| $N_2$ | −196 | | 15880 |
| $SF_6$ | −68 | 23.5 | 5950 |
| $CF_4$ | −128 | 159 | 5172 |
| $C_2F_6$ | −78 | 26.2 | 1273 |
| $CF_3OCF_3$ | −59 | 10.9 | 932 |
| n-$C_3F_8$ | −37 | 6.8 | 583 |
| $CF_3OC_2F_3$ | −21.5 | 3.9 | 316 |
| n-$C_4F_{10}$ | −2 | 2.2 | 212 |
| $C_2F_3OC_2F_5$ | −1 | 1.9 | 73 |
| $CF_3OC_2F_4OCF_3$ (perfluoromonoglyme) | 17 | 1.16 | 36 |
| n-$C_5F_{12}$ | 29 | 0.84 | 66 |
| $CF_3OC_2F_4OC_2F_3$ | 38.5 | 0.55 | 9.0 |
| n-$C_6F_{14}$ | 57 | 0.27 | 24 |

TABLE 1-continued

Otswald coefficients and vapor pressures at 25° C.

| filling gas | b. p., °C.[1] | $P_{F,sat}^3$ atm[2] | $L \times 10^6$ [3] |
|---|---|---|---|
| $C_3F_7OC_3F_7$ | 56 | 0.30 | 6.7 |
| $CF_3O(CF_2CF_2O)_2CF_3$ (perfluorodiglyme) | 64 | 0.20 | 0.9 |

[1]T. M. Reed, III, in: Fluorine Chemistry, J. H. Simons, Ed., V. 5, Academic Press, New York and London, 1964, p. 133; A. A. Woolf, J. Fluorine Chem., 63 (1993) 19; V. V. Berenblit, Yu. P. Dolnakov, V. P. Sass, L. N. Senyushov, and S. V . Sokolov, Zh. Org. Khim., 10 (1974) 2031, and experimental measurements.
[2]If not present in Refs. 1, calculated with the model of D. D. Lawson, J. Moacanin, K. V. Scherer, Jr, T. F. Terranova, and J. D. Ingham, J. Fluorine Chem., 12 (1978) 221.
[3]The first four values as reported by E. Wilhelm, R. Battino, and R. J. Wilcock, Chem. Rev., 77 (1977) 219. The others estimated as described in: A. S. Kabalnov, K. N. Makarov and E. V. Shcherbakova, J. Fluorine Chem., 50 (1990) 271.

Table 1 shows the solubilities, vapor pressures, and Ostwald coefficients of several compounds, including certain biocompatible fluorocarbons. Table 1 illustrates that perfluorobutane and perfluoropentane, which are gases at body temperature and atmospheric pressure, and which are contemplated as bubble gases by Quay and Schneider, have low Ostwald coefficients, and therefore also perform suitably as gas osmotic agents in conjunction with a primary modifier gas. However, the ability to consider candidate compounds which are liquids at body temperature and atmospheric pressure allows the selection of certain optimal low Ostwald coefficient compounds that have not previously been considered in any way suitable for microbubble preparations.

It should be remembered that Equation 7 is valid for bubbles containing gas combinations, where one of the gases is already present in the bloodstream, and where that gas (the "primary modifier gas") can diffuse across the gas/liquid interface much faster than the other gas (the "gas osmotic agent") in the combination. Only then is the partial pressure of the gas osmotic agent in the bubble equal to only the Laplace pressure rather than the total pressure inside the bubble. Because the Laplace pressure may be less than 1 atmosphere (at least for a large percentage of a bubble's lifetime) it is possible to use gas osmotic agents that are liquids at body temperature and atmospheric pressure. Such compounds would not form bubbles at all without the additional presence of the primary modifier gas.

On the other hand, although the gas osmotic agent can be a liquid at body temperature, its saturated vapor pressure must be large enough so that the Laplace pressure does not immediately force the gas osmotic agent in the bubble to condense into a liquid. The saturated vapor pressure of the gas osmotic agent is preferably larger than approximately 100 torr. Perfluorinated hydrocarbons, previously contemplated as microbubble filling gases have generally correlated water solubilities and saturated vapor pressures. That is, choosing a fluorocarbon with reduced water solubility also meant choosing a fluorocarbon with reduced saturated vapor pressure.

In this invention, we disclose a previously unconsidered class of compounds which combine a reduced water solubility without a significantly reduced saturated vapor pressure, and thus these compounds have surprisingly low Ostwald coefficients. These compounds are the fluorinated mono- and polyethers. Fluorinated mono- and polyethers are known to be safe and non-toxic. It is also known in the art (D. D. Lawson et al., *J. Fluorine Chem.* 12, p 221 (1978)) that these compounds have a very high vapor pressure and low boiling point at a given number of carbon atoms. Thus, the boiling point and saturated vapor pressure of a fluorinated polyether are almost the same as those of its fluorocarbon analogue with the same carbon number.

However, the water solubility, and thus the Ostwald coefficient, of the fluoroethers is lower than that of the fluorocarbon analogues—the value decreases by a factor of 2–3 with each oxygen atom added. Normally, it would be expected that the addition of an oxygen atom capable of hydrogen bonding to water would lead to an increase in solubility. It has been found experimentally that especially long lived contrast enhancement gas emulsions may be prepared when the gas bubbles contain air or nitrogen mixed with a fluoromono- or polyether. Accordingly, perfluorodiglyme, $CF_3(OCF_2CF_2)_2OCF_3$, perfluoromonoglyme, $CF_3OCF_2CF_2CF_3$, perfluorodiethylether, $C_2F_5OC_2F_5$, perfluoroethylmethylether, $CF_3OC_2F_5$, and perfluorodimethylether, $CF_3OCF_3$, have been found to be especially suitable gas osmotic agents.

A wide variety of fluorinated ethers have the above described properties which make them especially suitable as gas osmotic agents for stabilizing gas emulsions. Depending on the number of carbon atoms, the fluorinated ethers may be either gases or liquids at body temperature and atmospheric pressure. Those fluorinated ethers which are gases at body temperature and atmospheric pressure are also useful as the sole gaseous component of a gas emulsion preparation. A primary modifier gas, though improving the efficacy of gas emulsions made with all gas osmotic agents, is not required if the fluorinated ether used is a gas at body temperature and atmospheric pressure. Furthermore, useful fluorinated ether osmotic agents may be either completely or only partially fluorinated. Some of the fluorinated ethers which are useful as gas osmotic agents according to the present invention are: $CH_3CH_2OCF_2CHF_2$, $CH_3CH_2OCF_2CF_3$, $CHF_2CH_2OCF_2CHF_2$, $CF_3CH_2OCF_2CH_2F$, $CF_3CH_2OCH_2CF_3$, $CF_3CH_2OCF_2CHF_2$, $CHF_2CH_2OCF_2CF_3$, $CF_3CH_2OCF_2CF_3$, $CH_3OCH_2CF_2CHF_2$, $CH_3OCH_2CF_2CF_3$, $CH_3OCF_2CF_2CHF_2$, $CH_3OCF_2CHFCF_3$, $CH_3OCF_2CF_2CF_3$, $CHF_2OCH_2CF_2CHF_2$, $CHF_2OCH_2CF_2CF_3$, $CF_3OCH_2CF_2CHF_2$, $CF_3OCH_2CF_2CF_3$, $CH_3OCH(CF_3)_2$, $CH_3OCF(CF_3)_2$, $CHF_2OCH(CF_3)_2$, $CH_3OCH_2CHF_2$, $CH_3OCF_2CH_2F$, $CH_3OCH_2CF_3$, $CH_3OCF_2CHF_2$, $CHF_2OCH_2CHF_2$, $CHF_2OCF_2CH_2F$, $CHF_2OCH_2CF_3$, $CHF_2OCHFCF_3$, $CF_3OCH_2CHF_2$, $CH_3OCF_2CF_3$, $CF_3OCH_2CF_3$, $CF_3OCHFCF_3$.

Once a suitable low Ostwald coefficient gas is chosen, preferably a fluorinated ether, microbubbles incorporating the gas may be formed in a variety of ways, both with and without a shell or surfactant interfacial layer, as is described in detail below.

III. Microbubble Formation and Encapsulation

Microbubble preparation methods include the formation of particulate microspheres through the ultrasonication of albumin or other protein as described in European Patent Application 0,359,246 by Molecular Biosystems, Inc.; the use of tensides and viscosity increasing agents as described in U.S. Pat. No. 4,446,442; lipid coated, non-liposomal, microbubbles as is described in U.S. Pat. No. 4,684,479; liposomes having entrapped gases as is described in U.S. Pat. Nos. 5,088,499 and 5,123,414; and the use of denatured albumin particulate microspheres as is described in U.S. Pat. No. 4,718,433. The disclosure of each of the foregoing patents and applications is hereby incorporated by reference.

Sonication can be accomplished in a number of ways. For example, a vial containing a surfactant solution and gas in the headspace of the vial can be sonicated through a thin membrane. Preferably, the membrane is less than about 0.5 or 0.4 mm thick, and more preferably less than about 0.3 or even 0.2 mm thick, i.e., thinner than the wavelength of ultrasound in the material, in order to provide acceptable transmission and minimize membrane heating. The membrane can be made of materials such as rubber, Teflon, mylar, urethane, aluminized film, or any other sonically transparent synthetic or natural polymer film or film forming material. The sonication can be done by contacting or even depressing the membrane with an ultrasonic probe or with a focused ultrasound "beam." The ultrasonic probe can be disposable. In either event, the probe can be placed against or inserted through the membrane and into the liquid. Once the sonication is accomplished, the microbubble solution can be withdrawn from and vial and delivered to the patient.

Sonication can also be done within a syringe with a low power ultrasonically vibrated aspirating assembly on the syringe, similar to an inkjet printer. Also, a syringe or vial may be placed in and sonicated within a low power ultrasonic bath that focuses its energy at a point within the container.

Mechanical formation of microbubbles is also contemplated. For example, bubbles can be formed with a mechanical high shear valve (or double syringe needle) and two syringes, or an aspirator assembly on a syringe. Even simple shaking may be used. The shrinking bubble techniques described below are particularly suitable for mechanically formed bubbles, having lower energy input than sonicated bubbles. Such bubbles will typically have a diameter much larger than the ultimately desired biocompatible imaging agent, but can be made to shrink to an appropriate size in accordance with the present invention.

In another method, microbubbles can be formed through the use of a liquid osmotic agent emulsion supersaturated with a modifier gas at elevated pressure introduced into in a surfactant solution. This production method works similarly to the opening of soda pop, where the gas foams upon release of pressure forming the bubbles.

In another method, bubbles can be formed similar to the foaming of shaving cream, with perfluorobutane, freon, or another like material that boils when pressure is released. However, in this method it is desirable that the emulsified liquid boils sufficiently low or that it contain numerous bubble nucleation sites so as to prevent superheating and supersaturation of the aqueous phase. This supersaturation will lead to the generation of a small number of large bubbles on a limited number of nucleation sites rather than the desired large number of small bubbles (one for each droplet).

In the alternative, a lyophilized cake of surfactant and bulking reagents produced with a fine pore structure can be placed in a vial with a sterile solution and a head spaced with an osmotic gas mixture. The solution can be frozen rapidly to produce a fine ice crystal structure and, therefore, upon lyophilization produces fine pores (voids where the ice crystals were removed).

Alternatively, any dissolvable or soluble void-forming structures may be used. In this embodiment, where the void-forming material is not made from or does not contain surfactant, both surfactant and liquid are supplied into the container with the structures and the desired gas or gases. Upon reconstitution these voids trap the osmotic gas and, with the dissolution of the solid cake, form microbubbles with the gas or gases in them.

In still another method, dry void-containing particles or other structures (such as hollow spheres or honeycombs) that rapidly dissolve or hydrate, preferably in an aqueous solution, e.g., albumin, microfine sugar crystals, hollow spray dried sugar, salts, hollow surfactant spheres, dried porous polymer spheres, dried porous hyaluronic acid, or substituted hyaluronic acid spheres, or even commercially available dried lactose microspheres can be stabilized with a gas osmotic agent.

Preferably, gas emulsion compositions incorporating low Ostwald coefficient gases are prepared by spray drying an aqueous dispersion which contains a hydrophilic monomer or polymer or combination thereof. This procedure is also described in detail in co-pending U.S. patent application Ser. No. 08/405,477. In this case, a bubble forming composition is formed by spray drying an aqueous dispersion of a hydrophilic moiety such as starch, preferably also including a surfactant, to form a powder of dry, hollow, approximately microspherical porous shells of approximately 1 to 10 μm in diameter, with shell thicknesses of approximately 0.2 μm. Commercially available spray dryers are well known to those in the art, and suitable settings for any particular starch/surfactant dispersions can be readily determined through standard empirical testing, with due reference to the examples that follow. After formation, the desired gas is made to permeate the dry microspheres by placing the microspheres into a vial, evacuating the air, and replacing it with the desired gas or gas mixture.

The hydrophilic moiety in the solution to be spray dried can, for example, be a carbohydrate, such as glucose, lactose, or starch. Polymers such as PVA or PVP are also contemplated. Various starches and derivatized starches have been found to be especially suitable. Particularly preferred starches for use in formation of microbubbles include those with a molecular weight of greater than about 500,000 daltons or a dextrose equivalency (DE) value of less than about 12. The DE value is a quantitative measurement of the degree of starch polymer hydrolysis. It is a measure of reducing power compared to a dextrose standard of 100. The higher the DE value, the greater the extent of starch hydrolysis. Such preferred starches include food grade vegetable starches of the type commercially available in the food industry, including those sold under the trademarks N-LOK and CAPSULE by National Starch and Chemical Co., (Bridgewater, N.J.); derivatized starches, such as hydroxyethyl starch (available under the trademarks HETASTARCH and HESPAN from du Pont Pharmaceuticals, M-Hydroxyethylstarch from Ajinimoto, Tokyo, Japan). However, due to particularly advantageous stabilization characteristics, starches with a molecular weight of 500,000 or above are preferred (Note that short chain starches spray dry well and may be used to produce microbubbles in accordance with the present invention.) The hydrophilic monomer or polymer is present in this embodiment of the precursor solution at a range of about 0.1% to 10% w/v of solution, with about 1% to 5% w/v having been found to be especially suitable.

Preferably, the aqueous dispersion also includes a surfactant or mixture of surfactants, provided at about 0.01% to 20% w/v of solution. Many surfactants and surfactant mixtures are known and may be used. Surfactants may be selected from the group consisting of phospholipids, phosphocholines, lysophospholipids, nonionic surfactants, neutral or anionic surfactants, fluorinated surfactants, which can be neutral or anionic, and combinations of such emulsifying or foaming agents. Other specific examples of surfactants include block copolymers of polyoxypropylene and polyoxyethylene (an example of such class of compounds is Pluronic, such as Pluronic F-68), sugar esters, fatty alcohols, aliphatic amine oxides, hyaluronic acid aliphatic esters, hyaluronic acid aliphatic ester salts, dodecyl poly (ethyleneoxy)ethanol, nonylphenoxy poly(ethyleneoxy) ethanol, derivatized starches, hydroxy ethyl starch fatty acid esters, salts of fatty acids, commercial food vegetable starches, dextran fatty acid esters, sorbitol fatty acid esters, gelatin, serum albumins, and combinations thereof. Also contemplated are polyoxyethylene fatty acids esters, such as polyoxyethylene stearates, polyoxyethylene fatty alcohol ethers, polyoxyethylated sorbitan fatty acid esters, glycerol polyethylene glycol oxystearate, glycerol polyethylene glycol ricinoleate, ethoxylated soybean sterols, ethoxylated castor oils, and the hydrogenated derivatives thereof. In addition, nonionic alkylglucosides such as Tweens®, Spans® and Brijs® are also within the scope of the present invention. The Spans include sorbitan tetraoleate, sorbitan tetrastearate, sorbitan tristearate, sorbitan tripalmitate, sorbitan trioleate, and sorbitan distearate. Tweens include polyoxyethylene sorbitan tristearate, polyoxyethylene sorbitan tripalmitate, polyoxyethylene sorbitan trioleate. The Brij family is another useful category of materials, which includes polyoxyethylene 10 stearyl ether. Anionic surfactants, particularly fatty acids (or their salts) having 6 to 24 carbon atoms, may also be used. One example of a suitable anionic surfactant is oleic acid, or its salt, sodium oleate. Also suitable are cationic surfactants and their salts, such as dodecyltrimethylammonium chloride.

It will be appreciated from the foregoing that a wide range of surfactants can be used. Indeed, virtually any surfactant (including those still to be developed) or surfactant combination can be used in the present invention. The optimum surfactant for a given application can be determined through empirical studies that do not require undue experimentation. Consequently, one practicing the art of the present invention could select a surfactant primarily based properties such as biocompatibility.

It has been found especially suitable for the solution to contain a mixture of surfactants including a hydrophobic phospholipid as a first surfactant and at least one additional more hydrophilic second surfactant. Preferably, the hydrophobic phospholipid has at least one acyl chain with a total of at least about 10 carbon atoms (e.g. a didecanoyl phospholipid). In some embodiments, the phospholipid first surfactant will have acyl chains from about 10 or 14 to about 20 or 24 carbon atoms. For example, dipalmitoylphosphatidylcholine (comprising two acyl chains, each comprising 16 carbon atoms) may be used. The acyl chain may be hydrogenated or fluorinated. Other phospholipid head groups are also contemplated. For example, the phosphatidylserines, phosphatidylglycerols, or phosphatidylethanolamines will have properties suited to the present invention. Combinations of such phospholipids can also comprise the "first surfactant," as can naturally derived phospholipid products such as egg or soy lecithin, or lung surfactants. In addition, the phospholipid first surfactant may be supplemented with other highly water insoluble surfactants such as sucrose di-, tri-, and tetra-esters. Cholesterol may also supplement the first surfactant, and has been found useful in promoting stability when provided in a range from about 0.01 to 0.5 w/w cholesterol to phospholipid. Preferably, the acyl chains of the phospholipid are saturated, although unsaturated acyl groups are also within the scope of the present invention. The first surfactant is preferably provided in a range from about 0.005% to 20% w/v of the solution, most preferably in the range of 0.02% to 10% w/v.

It has been found to be advantageous to use a phospholipid mixture comprising a relatively hydrophobic long acyl chain phospholipid in combination with a shorter chain phospholipid which is more hydrophilic than the first phospholipid. As a specific example, a first phospholipid having acyl chains with 12 or 14 carbon atoms may be provided with a second phospholipid as a co-surfactant having acyl chains with eight or ten carbon atoms.

It has been found particularly advantageous to provide phospholipid comprising 12 carbon atom acyl chains as either the first or second surfactants. For example, a phospholipid with 12 carbon atom acyl chains may comprise the first surfactant, and a sugar ester or Pluronic compound can comprise the second surfactant. As another option, a phospholipid with 16 carbon atom acyl chains may comprise the first surfactant, and a phospholipid with 12 carbon atom acyl chains may comprise the second surfactant.

The spray dried product ultimately produced is a more effective bubble producer if an inflating agent, preferably a fluorocarbon such as Freon 113, is dispersed in the starch/surfactant solution described above. The inflating agent can be any material that will turn to a gas during the spray drying process. The inflating agent is dispersed throughout the surfactant solution, using, for instance, a commercially available microfluidizer at a pressure of about 5000 to 15,000 psi. This process forms a conventional emulsion comprised of submicron droplets of water immiscible Freon (or other inflating agent) coated with a monomolecular layer of surfactant. Dispersion with this and other techniques are common and well known to those in the art.

The inclusion of an inflating agent in the solution to be spray-dried results in a greater ultrasound signal per gram of spray-dried powder by forming a greater number of hollow microspheres. The inflating agent nucleates steam bubble formulation within the atomized droplets of the solution entering the spray dryer as these droplets mix with the hot air stream within the dryer. Suitable inflating agents are those that supersaturate the solution within the atomized droplets with gas or vapor, at the elevated temperature of the drying droplets (approximately 100° C.). Suitable agents include:

1. Dissolved low-boiling (below 100° C.) solvents with limited miscibility with aqueous solutions, such as methylene chloride, acetone and carbon disulfide used to saturate the solution at room temperature.

2. A gas, e.g. $CO_2$ or $N_2$, used to saturate the solution at room temperature and elevated pressure (e.g. 3 bar). The droplets are then supersaturated with the gas at 1 atmosphere and 100° C.

3. Emulsions of immiscible low-boiling (below 100° C.) liquids such as Freon 113, perfluoropentane, perfluorohexane, perfluorobutane, pentane, butane, FC-11, FC-11B1, FC-11B2, FC-12B2, FC-21, FC-21B1, FC-21B2, FC-31B1, FC-113A, FC-122, FC-123, FC-132, FC-133, FC-141, FC-141B, FC-142, FC-151, FC-152, FC-1112, FC-1121 and FC-1131.

Inflating agents are added to the starch/surfactant solution in quantities of about 0.5% to 10% v/v of the surfactant solution. Approximately 3% v/v inflating agent has been found to produce a spray dried powder which forms suitable microbubbles. The inflating agent is substantially evaporated during the spray drying process and thus is not present in the final spray-dried powder in more than trace quantities.

Other optional components of this solution are various salts or other agents within the aqueous phase. Such agents may advantageously include conventional viscosity modifiers, buffers such as phosphate buffers or other conventional biocompatible buffers or pH adjusting agents such as acids or bases, osmotic agents (to provide isotonicity, hyperosmolarity, or hyposmolarity). Preferred solutions have a pH of about 7 and are isotonic. These additional ingredients each typically comprise less than 5% w/v of solution. Examples of suitable salts include sodium phosphate (both monobasic and dibasic), sodium chloride, calcium phosphate, and other physiologically-acceptable salts.

After spray drying, the various individual components of the microspheres preferably comprise the following proportions of the final spray dried product in % by weight:

| Hydrophilic structural material | 1% to 100% |
| Surfactant | 0% to 90% |
| Salts, buffer, etc. | 0% to 90% |

In particularly preferred embodiments, the composition has the following proportions in % by weight:

| Hydrophilic structural material | 10% to 60% |
| Surfactant | 0.1% to 10% |
| Salts, buffer, etc. | 10% to 60% |

As mentioned above, the desired gas is made to permeate the dry microspheres by placing the microspheres into a vial, which is placed in a vacuum chamber to evacuate the air. The air is then replaced with the desired gas or gas mixture. The gas will then diffuse into the voids of the spheres. Diffusion can be aided by pressure or vacuum cycling. The vial is then crimp sealed and preferably sterilized with gamma radiation.

Preferably, the first primary modifier gas (which may be air or any of its component gases such as nitrogen) and the second osmotic stabilizer gas (preferably having low Ostwald coefficient) are respectively present in a molar ratio of about 1:100, 1:75, 1:50, 1:30, 1:20, or 1:10 to about 1000:1, 500:1, 250:1, 100:1, 75:1 or 50:1. In a particularly preferred embodiment, the gas is nitrogen that has been saturated with perfluorodiglyme at 20 degrees C.

IV. Packaging and Use

It will be appreciated that kits can be prepared for use in making the microbubble preparations of the present invention. These kits can include a container enclosing the gas or gases described above for forming the microbubbles, the liquid, and the surfactant. The container can contain all of the sterile dry components, and the gas, in one chamber, with the sterile aqueous liquid in a second chamber of the same container. Suitable two-chamber vial containers are available, for example, under the trademarks WHEATON RS177FLW or S-1702FL from Wheaton Glass Co., (Millville, N.J.). Another example is provided by the B-D HYPAK Liquid/Dry 5+5 ml Dual Chamber prefilled syringe system (Becton Dickinson, Franklin Lakes, N.J.; described in U.S. Pat. No. 4,613,326). The advantages of this system include:

1. Convenience of use;
2. The aqueous-insoluble gas osmotic agent is sealed in by a chamber of aqueous solution on one side and an extremely small area of elastomer sealing the needle on the other side; and
3. a filtration needle such as Monoject #305 (Sherwood Medical, St. Louis, Mo.) can be fitted onto the syringe at the time of manufacture to ensure that no undissolved solids are injected.

The use of the two chamber syringe to form microbubbles is described in Example VIII.

It may be appreciated by one of ordinary skill in the art that other two-chamber reconstitution systems capable of combining the spray dried powder with the aqueous solution in a sterile manner are also within the scope of the present invention. In such systems, it is particularly advantageous if the aqueous phase can be interposed between the water-insoluble osmotic gas and the environment, to increase shelf life of the product. Where a material necessary for forming the microbubbles is not already present in the container, it can be packaged with the other components of the kit, preferably in a form or container adapted to facilitate ready combination with the other components of the kit.

Examples of particular uses of the microbubbles of the present invention include perfusion imaging of the heart, the myocardial tissue, and determination of perfusion characteristics of the heart and its tissues during stress or exercise tests, or perfusion defects or changes due to myocardial infarction. Similarly, myocardial tissue can be viewed after oral or venous administration of drugs designed to increase the blood flow to a tissue. Also, visualization of changes in myocardial tissue due to or during various interventions, such as coronary tissue vein grafting, coronary angioplasty, or use of thrombolytic agents (TPA or streptokinase) can also be enhanced. As these contrast agents can be administered conveniently via a peripheral vein to enhance the visualization of the entire circulatory system, they will also aid in the diagnosis of general vascular pathologies and in the ability to monitor the viability of placental tissue ultrasonically.

It should also be emphasized that the present invention have applications beyond ultrasound imaging. Indeed, the invention is sufficiently broad to encompass the use of phospholipid-containing gas emulsions in any system, including nonbiological applications.

It will further be understood that other components can be included in the microbubble formulations of the present invention. For example, osmotic agents, stabilizers, chelators, buffers, viscosity modulators, air solubility modifiers, salts, and sugars can be added to modify the microbubble suspensions for maximum life and contrast enhancement effectiveness. Such considerations as sterility, isotonicity, and biocompatibility may govern the use of such conventional additives to injectable compositions. The use of such agents will be understood to those of ordinary skill in the art and the specific quantities, ratios, and types of agents can be determined empirically without undue experimentation.

Any of the microbubble preparations of the present invention may be administered to a vertebrate, such as a bird or a mammal, as a contrast agent for ultrasonically imaging portions of the vertebrate. Preferably, the vertebrate is a human, and the portion that is imaged is the vasculature of the vertebrate. In this embodiment, a small quantity of microbubbles (e.g., 0.1 ml/Kg [2 mg/Kg spray-dried powder] based on the body weight of the vertebrate) is introduced intravascularly into the animal. Other quantities of microbubbles, such as from about 0.005 ml/Kg to about 1.0 ml/Kg, can also be used. Imaging of the heart, arteries, veins, and organs rich in blood, such as liver and kidneys can be ultrasonically imaged with this technique.

V. EXAMPLES

The foregoing description will be more fully understood with reference to the following Examples. Such Examples, are, however, exemplary of preferred methods of practicing the present invention and are not limiting of the scope of the invention or the claims appended hereto.

Example I

Preparation of Microbubbles Through Sonication

Microbubbles with an average number weighted size of 5 microns were prepared by sonication of an isotonic aqueous phase containing 2% Pluronic F-68 and 1% sucrose stearate as surfactants, air as a modifier gas and perfluorohexane as the gas osmotic agent.

In this experiment, 1.3 ml of a sterile water solution containing 0.9% NaCl, 2% Pluronic F-68 and 1% sucrose stearate was added to a 2.0 ml vial. The vial had a remaining head space of 0.7 ml initially containing air. Air saturated with perfluorohexane vapor (220 torr of perfluorohexane with 540 torr of air) at 25 degrees C. was used to flush the headspace of the vial. The vial was sealed with a thin 0.22 mm polytetrafluoroethylene (PTFE) septum. The vial was turned horizontally, and a ⅛" (3 mm) sonication probe attached to a 50 watt sonicator model VC50, available from Sonics & Materials was pressed gently against the septum. In this position, the septum separates the probe from the solution. Power was then applied to the probe and the solution was sonicated for 15 seconds, forming a white solution of finely divided microbubbles, having an average number weighted size of 5 microns as measured by Horiba LA-700 laser light scattering particle analyzer.

Example II

Spray Drying of Phospholipid-containing Solution

One liter of the following solution was prepared in water for injection: 2.0% w/v Maltrin M-100 maltodextrin (Grain Processing Corp. Muscatine, Iowa), 0.95% w/v sodium chloride (Mallinckrodt, St. Louis, Mo.), 1.0% Superonic F-68 (Serva, Heidelberg, Germany), 1.0% w/v Ryoto Sucrose Stearate S-1670 (Mitsubishi-Kasei Food Corp., Tokyo, Japan), and 0.5% Lipoid E-100-3 hydrogenated phospholipid (Ludwigshafen, Germany).

This solution was then spray dried in a Niro Atomizer Portable Spray Dryer equipped with a two fluid atomizer (Niro Atomizer, Copenhagen, Denmark) employing the following settings:

| hot air flow rate | 39.5 CFM |
|---|---|
| inlet air temp. | 245° C. |
| outlet air temp. | 100° C. |
| atomizer air flow | 350 liters/min |
| liquid feed rate | 1 liter/hr |

The dry, hollow spherical product had a diameter between about 1 μM and about 15 μM and was collected at the cyclone separator as is standard for this dryer. Aliquots of powder (250 mg) were weighed into 10 ml tubing vials, evacuated and sparged with perfluorohexane-saturated nitrogen at 13° C. and sealed. The nitrogen was saturated with perfluorohexane by passing it through three perfluorohexane filled gas washing bottles immersed in a 13° C. water bath.

Upon reconstitution with 5 ml of water for injection, numerous bubbles were observed by light microscopy, ranging in size from 1 to 20 microns. The fact that many approximately 1 micron bubbles could be observed for an appreciable time demonstrates the added stability gained by including a phospholipid in the formula as an additional non-Newtonian viscoelastic surfactant.

Example III

Perfluorodiglyme Gas Emulsion with Sucrose Ester/Poloxamer Surfactant

One liter of each of the following two solutions was prepared with the following ingredients for injection:

Solution 1:

3.9% w/v m-HES hydroxyethylstarch (Ajinimoto, Tokyo, Japan)

3.25% w/v Sodium chloride (Mallinckrodt, St. Louis, Mo.)

2.83% w/v Sodium phosphate, dibasic (Mallinckrodt, St. Louis, Mo.)

0.42% w/v Sodium phosphate, monobasic (Mallinckrodt, St. Louis, Mo.)

Solution 2:

2.11% w/v Poloxamer 188 (BASF, Parsipany, N.J.)

0.32% w/v Ryoto Sucrose Stearate S-1670 (Mitsubishi-Kasei Food Corp., Tokyo, Japan)

0.16% w/v Ryoto Sucrose Stearate S-570 (Mitsubishi-Kasei Food Corp., Tokyo, Japan)

Solution 2 was added to high shear mixer and cooled in an ice bath. A coarse suspension of 30 ml of 1,1,2-trichlorotrifluoroethane (Freon 113; EM Science, Gibbstown, N.J.) was made in the 1 liter of solution 2. This suspension was emulsified using a Microfluidizer (Microfluidics Corporation, Newton, Mass.; model M-110F) at 10,000 psi, 5° C. for 5 passes. The resulting emulsion was added to solution 1. This mixture was then spray dried in a Niro Atomizer Portable Spray Dryer equipped with a two fluid atomizer (Niro Atomizer, Copenhagen, Denmark) employing the following settings:

| hot air flow rate | 31 CFM |
|---|---|
| inlet air temp. | 370° C. |
| outlet air temp. | 120° C. |
| atomizer air flow | 290 liters/min |
| emulsion feed rate | 1.5 liter/hr |

The dry, hollow spherical product had a diameter between about 1 μM and about 15 μM and was collected at the cyclone separator as is standard for this dryer. Aliquots of powder (200 mg) were weighed into 10 ml tubing vials, sparged with perfluorodiglyme-saturated nitrogen at 20° C. and sealed. The nitrogen was saturated with perfluorodiglyme by passing it through three perfluorodiglyme filled gas washing bottles immersed in a 20° C. water bath. The amount of perfluorodiglyme vapor per vial was 12–14 mg.

The vials were reconstituted with 5 ml water for injection after inserting an 18-gauge needle as a vent to relieve pressure as the water was injected, forming approximately $6 \times 10^8$ bubbles per ml which were stable in vitro for several days.

One ml of the resulting microbubble suspension was injected intravenously into an approximately 3 kg rabbit instrumented to monitor the Doppler ultrasound signal of its carotid artery. A 10 MHz flow cuff (Triton Technology Inc., San Diego, Calif.; model ES-10-20) connected to a System 6 Doppler flow module (Triton Technology Inc.) fed the RF doppler signal to a LeCroy 9410 oscilloscope (LeCroy, Chestnut Ridge, N.Y.). The root mean square (RMS) voltage of the signal computed by the oscilloscope was transferred to a computer and the resultant curve fitted to obtain peak echogenic signal intensity and half-life of the microbubbles in blood. Signals before contrast were less than 0.1 volts RMS.

60 seconds post injection, signal intensity was 1.1 V rms, with a decay constant of approximately 0.00859 s$^{-1}$.

Example IV

Perfluorodiglyme Gas Emulsion with Phospholipid/ Poloxamer Surfactant

One liter of each of the following two solutions was prepared with the following ingredients for injection:

Solution 1:

36 g m-HES hydroxyethylstarch (Ajinimoto, Tokyo, Japan)

30 g Sodium chloride (Mallinckrodt, St. Louis, Mo.)

26 g Sodium phosphate, dibasic (Mallinckrodt, St. Louis, Mo.)

3.9 g Sodium phosphate, monobasic (Mallinckrodt, St. Louis, Mo.)

Solution 2:

4.5 g Poloxamer 188 (BASF, Parsipany, N.J.)

4.5 g Dipalmitoyl phosphatidylcholine (Avanti Polar Lipids, Alabaster, Ala.)

Solution 2 was added to high shear mixer and cooled in an ice bath. A coarse suspension of 30 ml of 1,1,2-trichlorotrifluoroethane (Freon 113; EM Science, Gibbstown, N.J.) was made in the 1 liter of solution 2. This suspension was emulsified using a Microfluidizer (Microfluidics Corporation, Newton, Mass.; model M-110F) at 10,000 psi, 5° C. for 5 passes. The resulting emulsion was added to solution 1. This mixture was then spray dried in a Niro Atomizer Portable Spray Dryer equipped with a two fluid atomizer (Niro Atomizer, Copenhagen, Denmark) employing the following settings:

| | |
|---|---|
| hot air flow rate | 31 CFM |
| inlet air temp. | 325° C. |
| outlet air temp. | 120° C. |
| atomizer air flow | 290 liters/min |
| emulsion feed rate | 1.5 liter/hr |

The dry, hollow spherical product had a diameter between about 1 $\mu$M and about 15 $\mu$M and was collected at the cyclone separator as is standard for this dryer. Aliquots of powder (200 mg) were weighed into 10 ml tubing vials, sparged with perfluorodiglyme-saturated nitrogen at 20° C. and sealed. The nitrogen was saturated with perfluorodiglyme by passing it through three perfluorodiglyme filled gas washing bottles immersed in a 20° C. water bath. The amount of perfluorodiglyme vapor per vial was 12–14 mg.

The vials were reconstituted with 5 ml water for injection after inserting an 18-gauge needle as a vent to relieve pressure as the water was injected, forming approximately 3×10$^8$ bubbles per ml which were stable in vitro for several days.

One ml of the resulting microbubble suspension was injected intravenously into an approximately 3 kg rabbit instrumented to monitor the Doppler ultrasound signal of its carotid artery. A 10 MHz flow cuff (Triton Technology Inc., San Diego, Calif.; model ES-10-20) connected to a System 6 Doppler flow module (Triton Technology Inc.) fed the RF doppler signal to a LeCroy 9410 oscilloscope (LeCroy, Chestnut Ridge, N.Y.). The root mean square (RMS) voltage of the signal computed by the oscilloscope was transferred to a computer and the resultant curve fitted to obtain peak echogenic signal intensity and half-life of the microbubbles in blood. Signals before contrast were less than 0.1 volts RMS.

60 seconds post injection, signal intensity was 0.4 V rms, with a decay constant of approximately 0.01835 s$^{-1}$.

Example V

Perfluorodiglyme Gas Emulsion with Phospholipid Mixture Surfactant

One liter of each of the following two solutions was prepared with the following ingredients for injection:

Solution 1:

36 g m-HES hydroxyethylstarch (Ajinimoto, Tokyo, Japan)

30 g Sodium chloride (Mallinckrodt, St. Louis, Mo.)

26 g Sodium phosphate, dibasic (Mallinckrodt, St. Louis, Mo.)

3.9 g Sodium phosphate, monobasic (Mallinckrodt, St. Louis, Mo.)

Solution 2:

4.8 g Dipalmitoyl phosphatidylcholine (Avanti Polar Lipids, Alabaster, Ala.)

3.4 g Dioctanoyl phosphatidylcholine (Avanti Polar Lipids, Alabaster, Ala.)

Solution 2 was added to high shear mixer and cooled in an ice bath. A coarse suspension of 30 ml of 1,1,2-trichlorotrifluoroethane (Freon 113; EM Science, Gibbstown, N.J.) was made in the 1 liter of solution 2. This suspension was emulsified using a Microfluidizer (Microfluidics Corporation, Newton, Mass.; model M-110F) at 10,000 psi, 5° C. for 5 passes. The resulting emulsion was added to solution 1. This mixture was then spray dried in a Niro Atomizer Portable Spray Dryer equipped with a two fluid atomizer (Niro Atomizer, Copenhagen, Denmark) employing the following settings:

| | |
|---|---|
| hot air flow rate | 31 CFM |
| inlet air temp. | 325° C. |
| outlet air temp. | 120° C. |
| atomizer air flow | 290 liters/min |
| emulsion feed rate | 1.5 liter/hr |

The dry, hollow spherical product had a diameter between about 1 $\mu$M and about 15 $\mu$M and was collected at the cyclone separator as is standard for this dryer. Aliquots of powder (200 mg) were weighed into 10 ml tubing vials, sparged with perfluorodiglyme-saturated nitrogen at 13° C. and sealed. The nitrogen was saturated with perfluorodiglyme by passing it through three perfluorodiglyme filled gas washing bottles immersed in a 13° C. water bath. The amount of perfluorodiglyme vapor per vial was 12–14 mg.

The vials were reconstituted with 5 ml water for injection after inserting an 18-gauge needle as a vent to relieve pressure as the water was injected, forming approximately 2×10$^8$ bubbles per ml which were stable in vitro for several days.

One ml of the resulting microbubble suspension was injected intravenously into an approximately 3 kg rabbit instrumented to monitor the Doppler ultrasound signal of its carotid artery. A 10 MHz flow cuff (Triton Technology Inc., San Diego, Calif.; model ES-10-20) connected to a System 6 Doppler flow module (Triton Technology Inc.) fed the RF doppler signal to a LeCroy 9410 oscilloscope (LeCroy, Chestnut Ridge, N.Y.). The root mean square (RMS) voltage of the signal computed by the oscilloscope was transferred to a computer and the resultant curve fitted to obtain peak echogenic signal intensity and half-life of the microbubbles in blood. Signals before contrast were less than 0.1 volts RMS.

60 seconds post injection, signal intensity was 0.2 V rms, with a decay constant of approximately 0.00387 s$^{-1}$.

Example VI

Biocompatibility of Gas Emulsions Prepared from Mixed Long-Chain/Short-Chain Phospholipids One liter of the following emulsion was prepared for spray-drying as described in Example II:

3.6% w/v m-HES hydroxyethylstarch (Ajinimoto, Tokyo, Japan)

3.0% w/v Sodium chloride (Mallinckrodt, St. Louis, Mo.)

2.6% w/v Sodium phosphate dibasic (Mallinckrodt, St. Louis, Mo.)

0.39% w/v Sodium phosphate monobasic (Mallinckrodt, St. Louis, Mo.)

0.22% w/v Dipalmitoylphosphatidylcholine (Syngena Ltd., Cambridge, Mass.)

0.31% w/v Dioctanoylphosphatidylcholine (Avanti Polar Lipids Inc., Alabaster, Ala.)

3.0% v/v 1,1,2-Trichlorotrifluoroethane (Freon 113; EM Science, Gibbstown, N.J.)

At these ratios of dipalmitoylphosphatidylcholine to dioctanoylphosphatidylcholine the surfactants form mixed micelles only. Upon reconstitution with 5 ml water, approximately 51 million gas emulsion droplets per ml were observed, ranging in size from 1 to 20 microns. The first order decay constant of the echogenic signal of the gas emulsion in rabbits at a dose of 5 mg/kg was determined to be 0.0029 s$^{-1}$. This corresponds to an intravascular half-life of 4 minutes.

The gas emulsion was assayed for complement activation using an in-vitro C3a diagnostic kit supplied by Quidel Corp. (San Diego, Calif.). No difference between the gas emulsion and the negative control (saline) were observed, indicating that the gas emulsion does not activate complement. It is well known that naked microbubbles activate complement.

| Sample Tested | [C3a] (ng/ml) |
| --- | --- |
| Zymosan (positive control) | 43403 |
| Saline (negative control) | 604 |
| gas emulsion | 412 |

The gas emulsion was also assayed for changes in hemodynamics in anesthetized dogs at a dose of 20 mg/kg. No changes in mean arterial pressure or pulmonary artery pressure were observed. These results indicate that no hemodynamic effects are observed with the gas emulsion at 10–100 times the clinically relevant dose.

| Time (minutes) | Mean Arterial Pressure (mmHg) | Pulmonary Artery Pressure (mmHg) |
| --- | --- | --- |
| 0 | 109.4 | 13.3 |
| 1 | 109.2 | 14.2 |
| 2 | 110.4 | 14.1 |
| 5 | 115.0 | 14.3 |
| 10 | 117.9 | 15.7 |
| 60 | 111.0 | 13.2 |
| 90 | 120.9 | 13.6 |

Thus, excellent efficacy and biocompatibility are provided in the same gas emulsion formulation.

Example VII

Microbubble Formation Using Two Chamber Vial 800 mg of spray dried powder was weighed into the lower chamber of a 20 ml Wheaton RS-177FLW two chamber vial. The vial was flushed with perfluorohexane-saturated nitrogen at 13° C. before inserting the interchamber seal. The upper chamber was filled with 10 ml sterile water for injection. The upper chamber stopper was inserted so as to eliminate all air bubbles in the upper chamber. Upon depression of the upper stopper, the interchamber seal was forced into the lower chamber, allowing the water to flow into the lower chamber and reconstitute the powder. Numerous stable microbubbles were formed as demonstrated by light microscopy. This procedure demonstrates the convenience of this form of packaging and the elimination of the need to provide a vent to eliminate pressure buildup when the aqueous phase is added to the powder.

Example VIII

Microbubble Formation Using Two Chamber Syringe

One hundred mg of spray dried powder was weighed into a 5 ml+5 ml HYPAK Liquid/Dry dual chamber syringe (Becton Dickinson, Franklin Lakes, N.J.) and shaken into the powder (needle end) chamber. The interchamber seal was then positioned just above the bypass channel. A 5 $\mu$M filter-containing needle was then fitted on the syringe. The powder-containing chamber was then filled with the gas osmotic agent by placing the assembly in a vacuum chamber, evacuating and refilling the chamber with the gas osmotic agent, perfluorohexane-saturated nitrogen at 13° C. The filter needle allows the evacuation and refilling of the atmosphere in the powder-containing chamber. A sealing needle cover was then placed on the needle. The liquid chamber was then filled with 4 ml water for injection and the plunger was seated using a temporary vent (wire inserted between the glass syringe barrel and the plunger so as to eliminate all air bubbles.

To reconstitute, the needle sealing cover was removed to eliminate pressure buildup in the powder chamber. The plunger was then depressed, forcing the interchamber seal to the bypass position which allowed the water to flow around the interchamber seal into the powder-containing chamber. The plunger motion was stopped when all the water was in the powder chamber. The syringe was agitated to dissolve the powder. Excess gas and any large bubbles were expelled by holding the syringe, needle end up, and further depressing the plunger. The solution containing numerous stabilized microbubbles (as observed by light microscopy) was then expelled from the syringe by depressing the plunger to its limit.

Example IX

In Vivo Efficacy of Fluoroether Containing Gas Emulsions Versus Air and Fluoroalkane Containing Gas Emulsions One liter of the dispersion A was prepared and spray dried as described in Example III, and one liter of dispersions B and C were prepared and spray dried as described in Example V.

A. Sucrose Ester Microbubble Formulation ("AF0145" in Table)

36 g of m-HES hydroxyethylstarch (Ajinimoto, Tokyo, Japan)

30 g of Sodium chloride (Mallincrodt, St. Luis, Mo.)

26 g Sodium phosphate dibasic (Mallincrodt, St. Louis, Mo.)

3.9 g of Sodium phosphate, monobasic (Mallincrodt, St. Louis, Mo.)

4.5 g of Sucrose ester 11025003 (Alliance Pharmaceutical Corp., San Diego, Calif.)

19.5 g of Poloxamer 188 (BASF, Parsipany, N.J.)

30 ml of 1,2,2-Trichlorotrifluoroethane (Freon 113; EM Science, Gibbstown, N.J.)

Water: for injection: 490 ml

B. Phospholipid Mixture Microbubble Formulation ("24b" in Table)

36 g of m-HES hydroxyethylstarch (Ajinimoto, Tokyo, Japan)

30 g of Sodium chloride (Mallincrodt, St. Louis, Mo.)

26 g Sodium phosphate dibasic (Mallincrodt, St. Louis, Mo.)

3.9 g of Sodium phosphate, monobasic (Mallincrodt, St. Louis, Mo.)

4.5 g of Dimiristoyl phosphatidylcholine (Avanti Polar Lipids, Alabaster, Ala.)

4.5 g of Dioctanoyl phosphatidylcholine (Avanti Polar Lipids, Alabaster, Ala.)

5.8% v/v perfluorohexane (3M)

Water: for injection: 490 ml

C. Phospholipid Mixture Microbubble Formulation ("24f" in Table)

36 g of m-HES hydroxyethylstarch (Ajinimoto, Tokyo, Japan)

30 g of Sodium chloride (Mallincrodt, St. Louis, Mo.)

26 g Sodium phosphate dibasic (Mallincrodt, St. Louis, Mo.)

3.9 g of Sodium phosphate, monobasic (Mallincrodt, St. Louis, Mo.)

3.4 g of Dimiristoyl phosphatidylcholine (Avanti Polar Lipids, Alabaster, Ala.)

4.8 g of Dioctanoyl phosphatidylcholine (Avanti Polar Lipids, Alabaster, Ala.)

5.8% v/v perfluorohexane (3M)

Water: for injection: 490 ml 100 mg samples of the spray-dried powder were placed in 10-ml vials and gassed by perf luoroether-air mixture repeated evacuation-gassing cycles with the help of a syringe needle equipped with a three-way valve. As the filling gases, perfluorodimethyl ether (85%, Exfluor Research, Tex., Austin), perfluoro (methylethyl ether) (80%, Exfluor Research, Tex., Austin), perfluoro(diethyl ether) (90%, Strem Chemicals, Newburyport, Mass.), n-perfluoropropane and n-perfluorobutane (97%, PCR Incorporated) were used. The amount of perfluoroether and fluorocarbon vapors per vial is shown in the Table. After reconstituting with 5 ml of water, the bubbles were formed, which were stable in vitro for several days. Their echogenic properties in vivo were evaluated using a Pulsed Doppler Signal Enhancement Rabbit Model as described in Example III. The properties of the bubble dispersions summarized in the table below.

| Sample No. | Powder | Filling gas | Amount of osmotic filling gas per vial, mg/atm | Doppler signal, V, 100 s after injection | Doppler signal, 300 s after injection |
|---|---|---|---|---|---|
| 1 | 24f | $CF_3OCF_3$ | 16.5 mg/0.26 atm | 0.3 | 0.1 |
| 2 | 24f | $CF_3OC_2F_5$ | 38 mg/0.46 atm | 0.8 | 0.2 |
| 3 | 24f | $\eta$-$C_3F_8$ | 49.7 mg/0.65 atm | 0.6 | 0 |
| 4 | 24f | air | — | 0 | 0 |
| 5 | 24b | $C_2F_5OC_2F_5$ | 48.2 mg/0.46 atm | 1.25 | 0.6 |
| 6 | 24b | $\eta$-$C_4F_{10}$ | 50 mg/0.51 atm | 1.0 | 0.5 |
| 7 | AF0145 | $CF_3OC_2F_5$ | 41.7 mg/0.50 atm | 0.75 | 0.1 |
| 8 | AF0145 | air | — | 0 | 0 |

Figure 1:
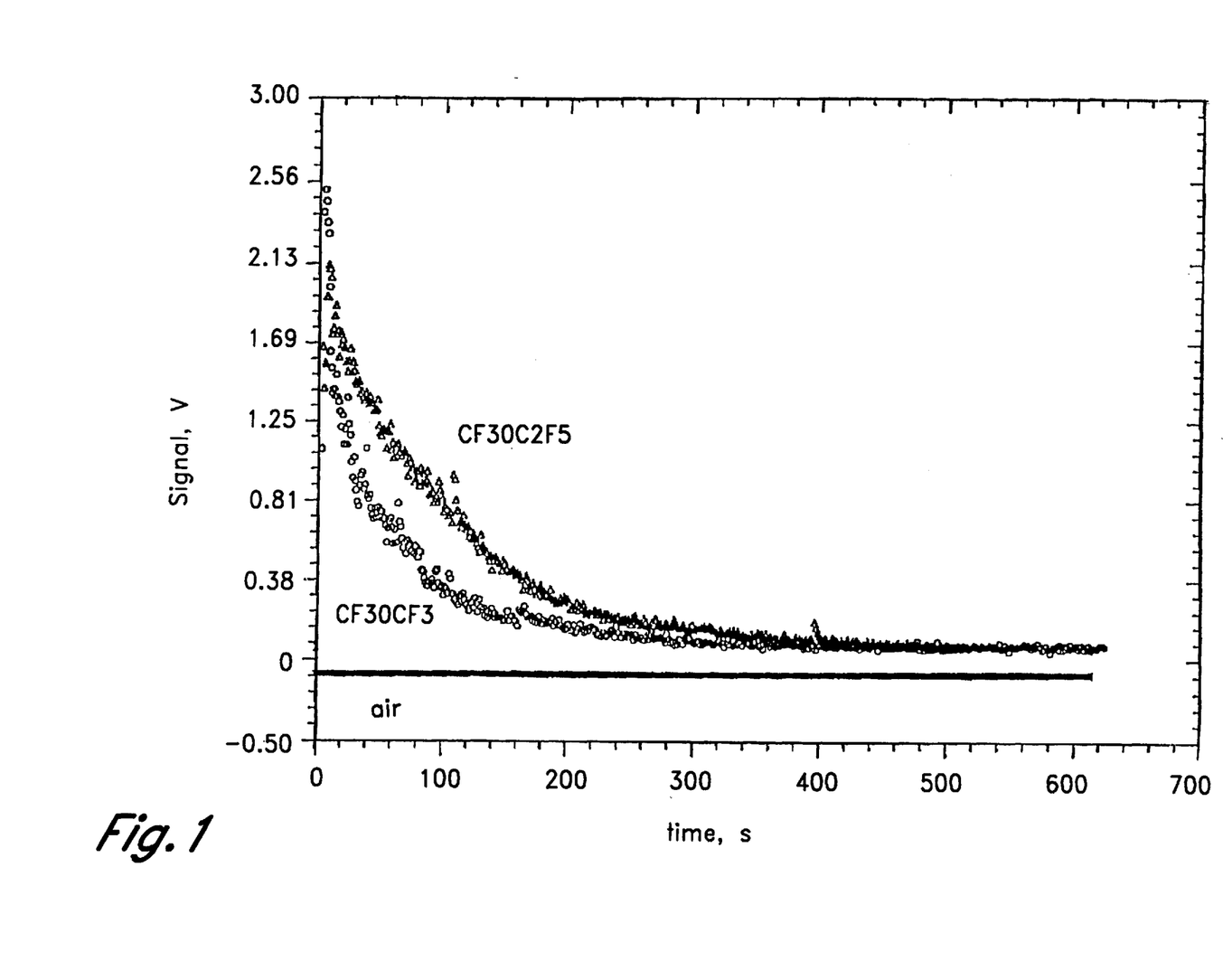
The FIGURE is a graph of in vivo pulsed Doppler signal intensity as a function of time from two fluoroether gas emulsions according to the present invention.

All the perfluoroether samples gave a significant ultrasound signal up to 300 s after injection into the bloodstream. The same preparations filled with air did not show any echogenicity 5 s after injection. Furthermore, perfluoroether-filled samples had a 20–30% better efficacy than their fluorocarbon analogues with the same number of carbon atoms, even when applied in smaller quantities. The figure illustrates the pulsed Doppler signal in volts as a function of time for experiments 1 and 2 shown in the above table.

Example X

In Vivo Echogenicity of Heart and Liver After Administration of Fluoroether Gas Emulsion Versus Fluoroalkane Containing Gas Emulsion Samples 2 and 3 as shown in the Table of Example IX were injected into an ear vein of a rabbit, after which the ultrasound scattered signal was measured by an ACUSON 128XP instrument with a 7 MHz transducer. Just after injection, both compositions led to a substantial contrasting-out of the blood vessels and the heart. This contrast gradually (at the timescale of several minutes) vanished and was replaced by contrasting out of liver, which lasted for ~10 min with perfluorobutane (sample 3) and ~15 min with perfluoro(methyl ethyl ether) (sample 2).

The present invention provides a stable gas dispersion or emulsion that is suitable for use as ultrasound and magnetic resonance imaging (MRI) contrast enhancement agents wherein the bubbles have a prolonged longevity in vivo. Typical ultrasound contrast enhancement agents only exhibit contrast enhancement potential for approximately one pass through the arterial system, or a few seconds to about a minute. Accordingly, such agents are not generally circulated past the aorta in a patient following intravenous injection. By comparison, stable contrast agents prepared in accordance with the present invention continue to demonstrate contrast enhancement duration sufficient for multiple passes through the entire circulatory system of a patient following intravenous injection. In vivo bubble lives of several minutes are easily demonstrated. Such lengthening of contrast enhancement potential during ultrasound is highly advantageous. In addition, the contrast enhancement agents of the invention provide superior imaging. For example, clear, vivid, and distinct images of blood flowing through the heart, liver, and kidneys are achieved. Thus small, nontoxic doses of the compositions of the present invention can be administered in a peripheral vein and used to enhance images of the entire body.

The foregoing description details certain preferred embodiments of the present invention and describes the best mode contemplated. It will be appreciated, however, that no matter how detailed the foregoing appears in text, the invention can be practiced in many ways and the invention should be construed in accordance with the appended claims and any equivalents thereof.

What is claimed is:

1. A gas emulsion for ultrasound contrast enhancement comprising a plurality of microbubbles in a liquid medium, said microbubbles comprising a gas or vapor selected from the group consisting of fluoromonoethers, fluoropolyethers, and mixtures thereof.

2. The composition of claim 1 wherein the gas or vapor is selected from the group consisting of perfluorodiethylether, perfluorodimethylether, perfluoromethylethylether, perfluoromonoglyme and perfluorodiglyme.

3. The composition of claim 1, wherein the microbubbles additionally comprises air or nitrogen.

4. The composition of claim 3, wherein the microbubbles additionally comprises air or nitrogen.

5. The gas emulsion of claim 1 wherein the microbubbles are surrounded by a surfactant layer.

6. The gas emulsion of claim 5, wherein the surfactant comprises at least a first and a second surfactant, the first surfactant consisting essentially of a phospholipid or mixture of phospholipids having at least one acyl chain which comprises at least 10 carbon atoms, and wherein the second surfactant is more water soluble than the first surfactant.

7. The gas emulsion of claim 6, wherein said second surfactant is selected from the group consisting of fatty acids, salts of a fatty acids, a sugar esters of fatty acids, polyoxypropylene-polyoxyethylene copolymers, nonionic alkylglucosides, polysorbate, and combinations thereof.

8. The gas emulsion of claim 6, wherein said second surfactant is selected from the group consisting of phospholipids, phosphocholine, lysophospholipid and combinations thereof wherein each acyl chain comprises no more than 14 carbon atoms.

9. The gas emulsion of claim 6, wherein said first surfactant comprises a phoshatidylcholine with one or more acyl chains, at least one chain comprising 12 to 18 carbon atoms, and said second surfactant comprises a phosphatidylcholine with one or more acyl chains, at least one chain comprising 6 to 12 carbon atoms.

10. A method for forming a gas emulsion comprising the steps of:

providing a container having therein a dry, hollow, particulate, approximately microspherical material comprising a surfactant, a hydrophilic monomer or polymer or combination thereof, and a gas or gas mixture comprising a compound with Ostwald coefficient of less than about $100 \times 10^{-6}$ at 37 degrees C.;

adding an aqueous liquid to said container; and, substantially dissolving said microspherical material in said aqueous liquid, thereby forming a gas emulsion in said container, said gas emulsion comprising bubbles of said gas or gas mixture surrounded by a layer of the surfactant.

11. The method of claim 10 wherein the gas comprises a fluoromono- or fluoropolyether vapor.

12. The method of claim 11 wherein the gas is selected from the group consisting of perfluorodiethylether vapor, perfluorodimethylether vapor, perfluoromethylethylether vapor, perfluoromonoglyme vapor and perfluorodiglyme vapor.

13. A method for forming a gas emulsion comprising the steps of:

providing a container having therein a dry, hollow, particulate, approximately microspherical material comprising a surfactant, a hydrophilic monomer or polymer or combination thereof, and a gas or gas mixture comprising a fluoromono- or fluoropolyether;

adding an aqueous liquid to said container; and, substantially dissolving said microspherical material in said aqueous liquid, thereby forming a gas emulsion in said container, said gas emulsion comprising bubbles of said gas or gas mixture surrounded by a layer of the surfactant.

14. The method of claim 13 wherein the gas is selected from the group consisting of perfluorodiethylether vapor, perfluorodimethylether vapor, perfluoromethylethylether vapor, perfluoromonoglyme vapor and perfluorodiglyme vapor.

15. A gas emulsion forming composition comprising:

a spray dried dispersion of a hydrophilic monomer or polymer or combination thereof, and a surfactant; and, a gas or gas mixture comprising a compound with Ostwald coefficient of less than about $500 \times 10^{-6}$ at 37 degrees C. in said container impregnated into said spray dried dispersion.

16. The composition of claim 15, wherein said surfactant comprises a phospholipid, a mixture of phospholipids, a phosphocholine, or a lysophospholipid.

17. A gas emulsion forming composition comprising:

a spray dried dispersion of a hydrophilic monomer or polymer or combination thereof, and a surfactant; and, a gas or gas mixture comprising a fluoromono- or fluoropolyether in said container impregnated into said spray dried dispersion.

18. The composition of claim 17, wherein said surfactant comprises a phospholipid, a mixture of phospholipids, a phosphocholine, or a lysophospholipid.

19. A method for ultrasonically imaging an object or body comprising the steps of:

introducing the contrast medium of claim 1 into said object or body; and, imaging at least a portion of said object or body.

20. The gas emulsion of claim 1 wherein said gas or vapor comprises a perfluoroether.

21. The gas emulsion of claim 20 wherein said perfluoroether is a perfluoropolyether.

22. The gas emulsion of claim 20 wherein said perfluoroether is a perfluoromonoether.

23. The gas emulsion of claim 1 wherein said gas or vapor comprises a polyether.

24. The gas emulsion of claim 1 wherein said gas or vapor comprises a monoether.

25. The gas emulsion of claim 1 wherein said gas or vapor is selected from the group consisting of $CH_3CH_2OCF_2CHF_2$, $CH_3CH_2OCF_2CF_3$, $CHF_2CH_2OCF_2CHF_2$, $CF_3CH_2OCF_2CH_2F$, $CF_3CH_2OCH_2CF_3$, $CF_3CH_2OCF_2CHF_2$, $CHF_2CH_2OCF_2CF_3$, $CF_3CH_2OCF_2CF_3$, $CH_3OCH_2CF_2CHF_2$, $CH_3OCH_2CF_2CF_3$, $CH_3OCF_2CF_2CHF_2$, $CH_3OCF_2CHFCF_3$, $CH_3OCF_2CF_2CF_3$, $CHF_2OCH_2CF_2CHF_2$, $CHF_2OCH_2CF_2CF_3$, $CF_3OCH_2CF_2CHF_2$, $CF_3OCH_2CF_2CF_3$, $CH_3OCH(CF_3)_2$, $CH_3OCF(CF_3)_2$, $CHF_2OCH(CF_3)_2$, $CH_3OCH_2CHF_2$, $CH_3OCF_2CH_2F$, $CH_3OCH_2CF_3$, $CH_3OCF_2CHF_2$, $CHF_2OCH_2CHF_2$, $CHF_2OCF_2CH_2F$, $CHF_2OCH_2CF_3$, $CHF_2OCHFCF_3$, $CF_3OCH_2CHF_2$, $CH_3OCF_2CF_3$, $CF_3OCH_2CF_3$, $CF_3OCHFCF_3$ and mixtures thereof.

26. The gas emulsion of claim 1 wherein said microbubbles further comprise microspheres.

27. The gas emulsion of claim 26 wherein said microspheres comprise a protein.

28. The gas emulsion of claim 1 wherein said microbubbles further comprise a liposome.

29. The gas emulsion of claim 1 wherein said microbubbles are formed through the solubilization of void containing structures.

30. The gas emulsion of claim 29 wherein said void containing structures comprise microspheres.

31. The gas emulsion of claim 30 wherein said microspheres comprise a compound selected from the group consisting of starches, derivatized starches and sugar esters.

32. The gas emulsion of claim 1 wherein said microbubbles are formed by altering the pressure on an emulsified liquid comprising an aqueous phase and a compound selected from the group consisting of fluoromonoethers, fluoropolyethers and mixtures thereof.

33. The gas emulsion of claim 1 wherein said microbubbles are formed through sonication.

34. The gas emulsion of claim 1 wherein said liquid medium comprises a viscosity enhancing agent.

35. The gas emulsion of claim 5 wherein said surfactant layer comprises a compound selected from the group consisting of nonionic surfactants, neutral surfactants, anionic surfactants, neutral fluorinated surfactants, anionic fluorinated surfactants and combinations thereof.

36. The gas emulsion of claim 5, wherein said surfactant is a non-Newtonian surfactant.

37. The gas emulsion of claim 5 wherein said surfactant layer comprises a compound selected from the group consisting of phospholipids, fatty acids, block copolymers and sugar esters.

38. A microbubble composition for use in imaging comprising a plurality of microbubbles in a biocompatible liquid medium, said microbubbles comprising a perfluoroether in a gaseous or vaporous state.

39. The microbubble composition of claim 38 wherein said perfluoroether is a perfluoropolyether.

40. The microbubble composition of claim 38 wherein said perfluoroether is a perfluoromonoether.

41. The microbubble composition of claim 38 wherein said perfluoroether is selected from the group consisting of perfluorodiethylether, perfluorodimethylether, perfluoromethylethylether, perfluoromonoglyme, perfluorodiglyme and mixtures thereof.

42. The microbubble composition of claim 38 wherein said microbubbles further comprise microspheres.

43. The microbubble composition of claim 42 wherein said microspheres comprise a protein.

44. The microbubble composition of claim 38 wherein said microbubbles further comprise a liposome.

45. The microbubble composition of claim 38 wherein said microbubbles are formed through the solubilization of void containing structures.

46. The microbubble composition of claim 45 wherein said void containing structures comprise microspheres.

47. The microbubble composition of claim 46 wherein said microspheres comprise a compound selected from the group consisting of starches, derivatized starches and sugar esters.

48. The microbubble composition of claim 38 wherein said microbubbles are formed by altering the pressure on an emulsified liquid comprising an aqueous phase and said perfluoroether.

49. The microbubble composition of claim 38 wherein said microbubbles are formed through sonication.

50. The microbubble composition of claim 38 wherein said liquid medium comprises a viscosity enhancing agent.

51. The microbubble composition of claim 38 wherein said microbubbles further comprise a surfactant layer.

52. The microbubble composition of claim 51 wherein said surfactant layer comprises a compound selected from the group consisting of nonionic surfactants, neutral surfactants, anionic surfactants, neutral fluorinated surfactants, anionic fluorinated surfactants and combinations thereof.

53. The microbubble composition of claim 51, wherein said surfactant layer comprises a non-Newtonian surfactant.

54. The microbubble composition of claim 51 wherein said surfactant layer comprises a compound selected from the group consisting of phospholipids, fatty acids, block copolymers and sugar esters.

55. A microbubble composition for use in imaging comprising a plurality of microbubbles in a biocompatible liquid medium wherein said microbubbles comprise at least one fluoroether gas osmotic agent and at least one modifier gas.

56. The microbubble composition of claim 55 wherein said fluoroether gas osmotic agent comprises a perfluoroether.

57. The microbubble composition of claim 56 wherein said perfluoroether is a perfluoropolyether.

58. The microbubble composition of claim 56 wherein said perfluoroether is a perfluoromonoether.

59. The microbubble composition of claim 55 wherein said fluoroether gas osmotic agent comprises a monoether.

60. The microbubble composition of claim 55 wherein said fluoroether gas osmotic agent comprises a polyether.

61. The microbubble composition of claim 55 wherein said fluoroether gas osmotic agent is selected from the group consisting of $CH_3CH_2OCF_2CHF_2$, $CH_3CH_2OCF_2CF_3$, $CHF_2CH_2OCF_2CHF_2$, $CF_3CH_2OCF_2CH_2F$, $CF_3CH_2OCH_2CF_3$, $CF_3CH_2OCF_2CHF_2$, $CHF_2CH_2OCF_2CF_3$, $CF_3CH_2OCF_2CF_3$, $CH_3OCH_2CF_2CHF_2$, $CH_3OCH_2CF_2CF_3$, $CH_3OCF_2CF_2CHF_2$, $CH_3OCF_2CHFCF_3$, $CH_3OCF_2CF_2CF_3$, $CHF_2OCH_2CF_2CHF_2$, $CHF_2OCH_2CF_2CF_3$, $CF_3OCH_2CF_2CHF_2$, $CF_3OCH_2CF_2CF_3$, $CH_3OCH(CF_3)_2$, $CH_3OCF(CF_3)_2$, $CHF_2OCH(CF_3)_2$, $CH_3OCH_2CHF_2$, $CH_3OCF_2CH_2F$, $CH_3OCH_2CF_3$, $CH_3OCF_2CHF_2$, $CHF_2OCH_2CHF_2$, $CHF_2OCF_2CH_2F$, $CHF_2OCH_2CF_3$, $CHF_2OCHFCF_3$, $CF_3OCH_2CHF_2$, $CH_3OCF_2CF_3$, $CF_3OCH_2CF_3$, $CF_3OCHFCF_3$ and mixtures thereof.

62. The microbubble composition of claim 55 wherein said microbubbles further comprise microspheres.

63. The microbubble composition of claim 62 wherein said microspheres comprise a protein.

64. The microbubble composition of claim 55 wherein said microbubbles further comprise a liposome.

65. The microbubble composition of claim 55 wherein said microbubbles are formed through the solubilization of void containing structures.

66. The microbubble composition of claim 65 wherein said void containing structures comprise microspheres.

67. The microbubble composition of claim 66 wherein said microspheres comprise a compound selected from the group consisting of starches, derivatized starches and sugar esters.

68. The microbubble composition of claim 55 wherein said microbubbles are formed by altering the pressure on an emulsified liquid comprising an aqueous phase and said fluoroether gas osmotic agent.

69. The microbubble composition of claim 55 wherein said microbubbles are formed through sonication.

70. The microbubble composition of claim 55 wherein said liquid medium comprises a viscosity enhancing agent.

71. The microbubble composition of claim 55 wherein said microbubbles further comprise a surfactant layer.

72. The microbubble composition of claim 71 wherein said surfactant layer comprises a compound selected from the group consisting of nonionic surfactants, neutral surfactants, anionic surfactants, neutral fluorinated surfactants, anionic fluorinated surfactants a nd combinations thereof.

73. The microbubble composition of claim 71, wherein said surfactant layer comprises a non-Newtonian surfactant.

74. The microbubble composition of claim 71 wherein said surfactant layer comprises a compound selected from the group consisting of phospholipids, fatty acids, block copolymers and sugar esters.

75. The microbubble composition of claim 55 wherein said modifier gas comprises oxygen.

76. The microbubble composition of claim 55 wherein said modifier gas comprises nitrogen.

77. A method for ultrasonically imaging an object or body comprising the steps of: introducing the contrast medium of claim 5 into said object or body; and, imaging at least a portion of said object or body.

78. A method for ultrasonically imaging an object or body comprising the steps of:

introducing the contrast medium of claim 29 into said object or body; and, imaging at least a portion of said object or body.

79. A method for ultrasonically imaging an object or body comprising the steps of:

introducing the contrast medium of claim 37 into said object or body; and, imaging at least a portion of said object or body.

80. A method for ultrasonically imaging an object or body comprising the steps of:

introducing the contrast medium of claim 38 into said object or body; and, imaging at least a portion of said object or body.

81. A method for ultrasonically imaging an object or body comprising the steps of:

introducing the contrast medium of claim 46 into said object or body; and, imaging at least a portion of said object or body.

82. A method for ultrasonically imaging an object or body comprising the steps of;

introducing the contrast medium of claim 55 into said object or body; and, imaging at least a portion of said object or body.

83. The composition of claim 56 wherein said modifier gas is selected from the group consisting of nitrogen, oxygen, carbon dioxide and mixtures thereof.

84. A method for ultrasonically imaging an object or body comprising the steps of:

introducing the contrast medium of claim 79 into said object or body; and, imaging at least a portion of said object or body.

85. A method for ultrasonically imaging an object or body comprising the steps of:

introducing the contrast medium of claim 67 into said object or body, and, imaging at least a portion of said object or body.

86. The composition of claim 67 wherein said modifier gas is selected from the group consisting of nitrogen, oxygen, carbon dioxide and mixtures thereof.

87. A method for ultrasonically imaging an object or body comprising the steps of introducing the contrast medium of claim 74 into said object or body; and, imaging at least a portion of said object or body.

88. The composition of claim 74 wherein said modifier gas is selected from the group consisting of nitrogen, oxygen, carbon dioxide and mixtures thereof.

89. A method for ultrasonically imaging an object or body comprising the steps of:

introducing the contrast medium of claim 76 into said object or body; and, imaging at least a portion of said object or body.

* * * * *